(12) United States Patent
Downey

(10) Patent No.: US 11,337,718 B2
(45) Date of Patent: May 24, 2022

(54) SYSTEM AND METHOD FOR CONTROLLING AN ULTRASONIC TOOL

(71) Applicant: Stryker Corporation, Kalamazoo, MI (US)

(72) Inventor: Adam Darwin Downey, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 17/154,324

(22) Filed: Jan. 21, 2021

(65) Prior Publication Data

US 2021/0137552 A1    May 13, 2021

Related U.S. Application Data

(63) Continuation of application No. 15/742,361, filed as application No. PCT/US2016/042193 on Jul. 14, 2016, now Pat. No. 10,945,753.

(Continued)

(51) Int. Cl.
*A61B 17/32* (2006.01)
*A61B 17/00* (2006.01)

(52) U.S. Cl.
CPC ............. *A61B 17/320068* (2013.01); *A61B 2017/0015* (2013.01); *A61B 2017/00017* (2013.01); *A61B 2017/00154* (2013.01)

(58) Field of Classification Search
CPC .. A61B 17/320068; A61B 2017/00017; A61B 2017/0015; A61B 2017/00154

(Continued)

(56) References Cited

U.S. PATENT DOCUMENTS

| 4,094,320 A | 6/1978 | Newton et al. |
| 4,231,372 A | 11/1980 | Newton |

(Continued)

FOREIGN PATENT DOCUMENTS

| CN | 202223769 U | 5/2012 |
| CN | 102497827 A | 6/2012 |

(Continued)

OTHER PUBLICATIONS

English language abstract and machine-assisted English Translation for CN 202223769 extracted from espacenet.com database on Jan. 11, 2021, 12 pages.

(Continued)

*Primary Examiner* — Jermele M Hollington
*Assistant Examiner* — Courtney G McDonnough
(74) *Attorney, Agent, or Firm* — Howard & Howard Attorneys PLLC

(57) ABSTRACT

Systems (10) and methods (12) of controlling an ultrasonic surgical tool (20) with a console (22) are provided. A first drive signal (40) is applied to the ultrasonic surgical tool (20). A characteristic of a harmonic signal (44) resulting from application of the first drive signal (40) to the ultrasonic surgical tool (20) is acquired. A cancellation signal (70) is generated based on the characteristic of the harmonic signal (44). The first drive signal (40) and the cancellation signal (70) are combined to produce a second drive signal (80) that is sinusoidal. The second drive signal (80) is applied to the ultrasonic surgical tool (20) such that presence of the harmonic signal (44) resulting from application of the second drive signal (80) is reduced relative to presence of the harmonic signal (44) resulting from application of the first drive signal (40).

16 Claims, 10 Drawing Sheets

Related U.S. Application Data

(60) Provisional application No. 62/192,838, filed on Jul. 15, 2015.

(58) Field of Classification Search
USPC ...... 324/623; 606/169, 27–50; 73/1.82, 703, 73/704
See application file for complete search history.

(56) References Cited

U.S. PATENT DOCUMENTS

| | | | |
|---|---|---|---|
| 5,152,762 | A | 10/1992 | McElhenney |
| 5,345,375 | A | 9/1994 | Mohan |
| 5,372,596 | A | 12/1994 | Klicek et al. |
| 8,475,446 | B2 | 7/2013 | Daw et al. |
| 8,551,088 | B2 | 10/2013 | Falkenstein et al. |
| 8,624,606 | B2 | 1/2014 | Gilbert |
| 8,852,182 | B2 | 10/2014 | Tullis et al. |
| 8,956,349 | B2 | 2/2015 | Aldridge et al. |
| 9,022,935 | B2 | 5/2015 | Akagane |
| 9,634,773 | B2 | 4/2017 | Deng et al. |
| 2009/0243398 | A1 | 10/2009 | Yohanan et al. |
| 2011/0087256 | A1 | 4/2011 | Wiener et al. |
| 2011/0092886 | A1 | 4/2011 | Raney et al. |
| 2012/0071796 | A1 | 3/2012 | Smith et al. |
| 2012/0078139 | A1 | 3/2012 | Aldridge et al. |
| 2012/0265196 | A1 | 10/2012 | Turner et al. |
| 2013/0282039 | A1 | 10/2013 | Wiener et al. |
| 2014/0225476 | A1 | 8/2014 | Degertekin et al. |
| 2016/0302848 | A1 | 10/2016 | Krapohl |
| 2017/0146584 | A1 | 5/2017 | Daw et al. |
| 2017/0151011 | A1 | 6/2017 | Brustad et al. |
| 2019/0083124 | A1 | 3/2019 | Downey |

FOREIGN PATENT DOCUMENTS

| | | |
|---|---|---|
| CN | 104052407 A | 9/2014 |
| CN | 104080417 A | 10/2014 |
| EP | 2283788 A1 | 2/2011 |
| GB | 2521229 A | 6/2015 |
| JP | H1052411 A | 2/1998 |
| WO | 2011008672 A2 | 1/2011 |
| WO | 2014096789 A2 | 6/2014 |
| WO | 2015099656 A1 | 7/2015 |

OTHER PUBLICATIONS

English language abstract for CN 102497827 extracted from espacenet.com database on Jan. 11, 2021, 2 pages.

English language abstract for CN 104052407 extracted from espacenet.com database on May 27, 2020, 2 pages.

English language abstract for CN 104080417 extracted from espacenet.com database on May 27, 2020, 1 page.

International Search Report for Application No. PCT/US2016/042193 dated Nov. 28, 2016, 2 pages.

English language abstract and machine-assisted English Translation for JPH 10-52411 A extracted from espacenet.com database on Dec. 28, 2021, 11 pages.

First Drive Signal Output

Handpiece Voltage and Current Before Harmonic Cancellation Technique

FFT of HP Voltage
Before Harmonic Cancellation Technique

FFT of HP Current
Before Harmonic Cancellation Technique

FFT of Handpiece Current Showing Harmonic Distortion

Handpiece Current with Fundamental and Harmonic Frequency Components

Fundamental Component of Handpiece Voltage in Isolation

Harmonic Frequency Component of Handpiece Current in Isolation

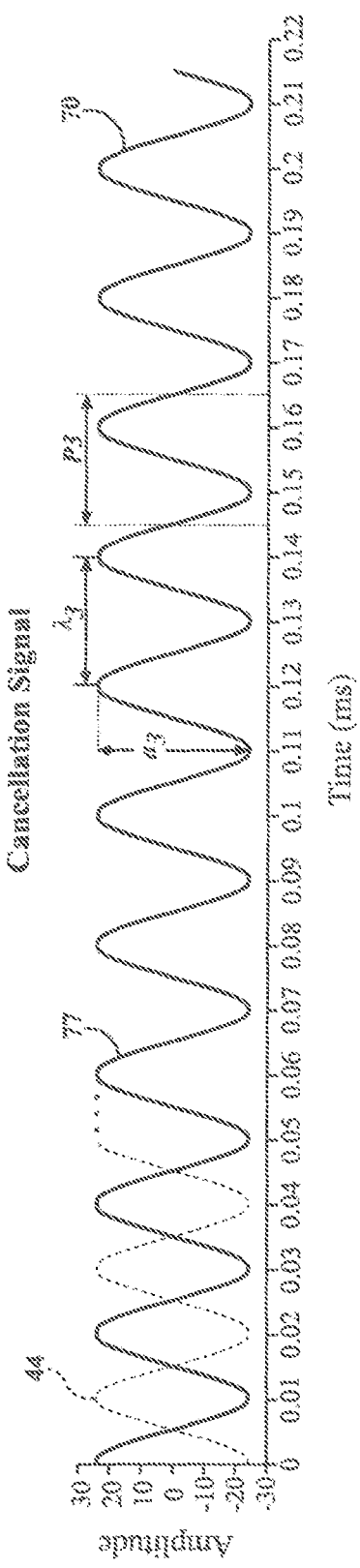
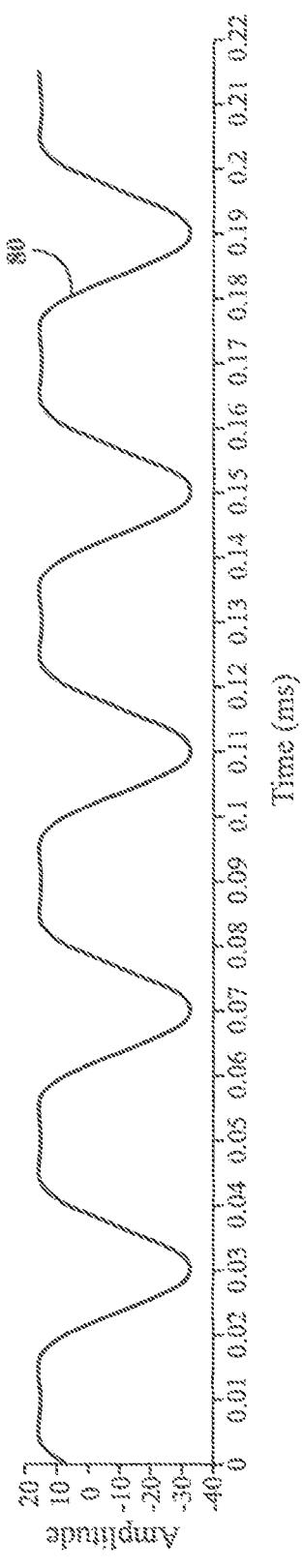

FFT of HP Voltage
After Harmonic Cancellation Technique

FFT of HP Current
After Harmonic Cancellation Technique

Handpiece Voltage and Current After Harmonic Cancellation Technique

FIG. 19

Comparison of Handpiece/Tip Control Parameters Before and After Harmonic Cancellation Technique

|  | Before | After | Difference | % Change |
|---|---|---|---|---|
| Mechanical Current | 80 mA | 80 mA | 0 | 0 |
| HP Voltage | 28.3 V | 21.9 V | -6.4 V | -23% |
| HP Current | 80 mA | 80 mA | 0 | 0 |
| HP Power | 1.13 W | 0.877 W | -0.253 W | -22% |
| [Z] Handpiece | 353.4 Ω | 273.7 Ω | -79.7 Ω | -23% |
| 51kHz Current Relative Magnitude | 0.08 | 0.0094 | na | 98.8% |

SYSTEM AND METHOD FOR CONTROLLING AN ULTRASONIC TOOL

CROSS-REFERENCE TO RELATED APPLICATION(S)

The present application is a continuation of U.S. patent application Ser. No. 15/742,361, filed Jan. 5, 2018, which is a national stage entry of PCT Application No. PCT/US2016/042193, filed Jul. 14, 2016, which claims the benefit of Provisional Patent Application No. 62/192,838, filed Jul. 15, 2015, the disclosures of which are hereby incorporated by reference herein in their entirety.

TECHNICAL FIELD

The present invention relates generally to a system and method for controlling an ultrasonic surgical tool, and more specifically, reducing presence of an unwanted signal resulting from operation of the surgical tool.

BACKGROUND

Ultrasonic surgical tools, such as ultrasonic aspirators, typically include a handpiece containing an ultrasonic transducer and a tip coupled to the transducer to interface with tissue. A console or generator is connected to the surgical tool to control the surgical tool by outputting specific drive signals to the transducer. The surgical tool is for use in open or minimally invasive surgical procedures to provide coagulation of tissue, and the like.

For many tip/transducer combinations, the transducer is driven with a sinusoidal drive signal that has a frequency component. The ultrasonic tip is typically designed to operate at the frequency component with only a single dominant vibration mode (e.g. longitudinal).

Vibrational motion of the tip is directly related to what in industry is referred to as mechanical current. The tip operates at resonance when mechanical current is in phase with the handpiece voltage. Since the transducer is driven with a sinusoidal signal with a frequency component, the current to the handpiece consequently is sinusoidal with a frequency component.

Some conventional ultrasonic tip and handpiece combinations naturally exhibit a harmonic signal or signals causing harmonic distortion. Such harmonic signals may cause the current to the handpiece to exhibit a variable phase shift relative to the voltage to the handpiece. In conventional systems, significant harmonic distortion is present in both the voltage and current to the handpiece. The harmonic signals cause the voltage and current to the handpiece to exhibit additional frequency components, such as harmonics, causing the voltage and current waveforms to be impurely sinusoidal. Such harmonics produce unwanted vibrations of the tip. The unwanted vibrations have a negative impact on the performance of the surgical tool. For example, such unwanted vibrations increase the stress on the tip and create unwanted excessive heat in certain locations. Such unwanted excessive heat reduces life of the tip due to fatigue and thermal heating of surrounding tissue. Furthermore, the system must operate at a higher voltage to overcome additional loading effects of the acoustical properties of the tip changing due to an increased temperature resulting from the excessive heat. In turn, performance of the controlling console is reduced because the unwanted vibration energy is sent back to the console from the handpiece.

SUMMARY

Accordingly, the present invention provides a console for controlling an ultrasonic surgical tool to reduce presence of a harmonic signal resulting from driving the ultrasonic surgical tool. The console is configured to apply a first drive signal to the ultrasonic surgical tool. The console acquires a characteristic of the harmonic signal resulting from application of the first drive signal to the ultrasonic surgical tool. The console generates a cancellation signal based on the characteristic of the harmonic signal. The console combines the first drive signal and the cancellation signal to produce a second drive signal, wherein the second drive signal is sinusoidal. The console is configured to apply the second drive signal to the ultrasonic surgical tool such that presence of the harmonic signal resulting from application of the second drive signal is reduced relative to presence of the harmonic signal resulting from application of the first drive signal.

The present invention also provides a method of controlling the ultrasonic surgical tool to reduce presence of the harmonic signal resulting from driving the ultrasonic surgical tool. The method includes driving the ultrasonic surgical tool with the first drive signal. The characteristic of the harmonic signal resulting from driving the ultrasonic surgical tool with the first drive signal is acquired. The method includes generating the cancellation signal based on the characteristic of the harmonic signal. The first drive signal and the cancellation signal are combined to produce the second drive signal wherein the second drive signal is sinusoidal. The method includes driving the ultrasonic surgical tool with the second drive signal such that presence of the harmonic signal resulting from driving the ultrasonic surgical tool with the second drive signal is reduced relative to presence of the harmonic signal resulting from driving the ultrasonic surgical tool with the first drive signal.

In addition, the present invention provides a method of controlling the ultrasonic surgical tool to reduce presence of the harmonic signal. The harmonic signal includes a frequency, phase, and amplitude. The method includes driving the ultrasonic surgical tool with a first drive signal, acquiring a characteristic of the harmonic signal resulting from driving the ultrasonic surgical tool with the first drive signal, and generating a cancellation signal with a frequency similar to the frequency of the harmonic signal, a phase that is shifted 180 degrees in relation to the phase of the harmonic signal, and an amplitude being equal to or greater than the harmonic signal. The method further includes outputting a second drive signal to drive the ultrasonic surgical tool wherein the second drive signal is sinusoidal and based on a combination of the first drive signal and the cancellation signal.

The system and method may advantageously reduce presence of the harmonic signal, thereby reducing harmonic distortion occurring from vibration of the surgical tool. By reducing presence of the harmonic signal, the system and method may effectively reduce impedance of the surgical tool, i.e., the handpiece/tip combination, the power and the voltage required for maintaining a specific vibrational displacement of the tip, heating of the tip, the energy being sent back to console, and/or the unwanted (e.g., harmonic) vibration frequency. These modifications, in turn, may improve tissue resection performance of the surgical tool.

Furthermore, by reducing the negative effects of the harmonic signal, the system and method increase versatility to use various types and shapes of ultrasonic tools and tips often exhibiting harmonic distortion. The system and method further allow simultaneous control over two different resonant modes of the tip to increase the cutting performance (e.g. bi-modal control).

Other features and advantages of the present invention will be readily appreciated, as the same becomes better understood, after reading the subsequent description.

BRIEF DESCRIPTION OF THE DRAWINGS

FIG. 14 is a chart of the waveform of a cancellation signal configured to reduce the harmonic frequency component of FIG. 13.

FIG. 15 is a chart illustrating a waveform of the output of a second drive signal applied by the console with the second drive signal generated based on a combination of the fundamental frequency component (first drive signal) of FIG. 12 and the cancellation signal of FIG. 14.

FIG. 19 is a table demonstrating the advantageous effects of the method on important parameters of controlling the handpiece and tip combination.

DETAILED DESCRIPTION

I. System Overview

Referring to the Figures, wherein like numerals indicate like or corresponding parts throughout the several views, aspects of a system 10 and method 12 for controlling an ultrasonic surgical tool 20 to reduce presence of a harmonic signal resulting from driving the ultrasonic surgical tool 20 are shown throughout.

Figure 1:
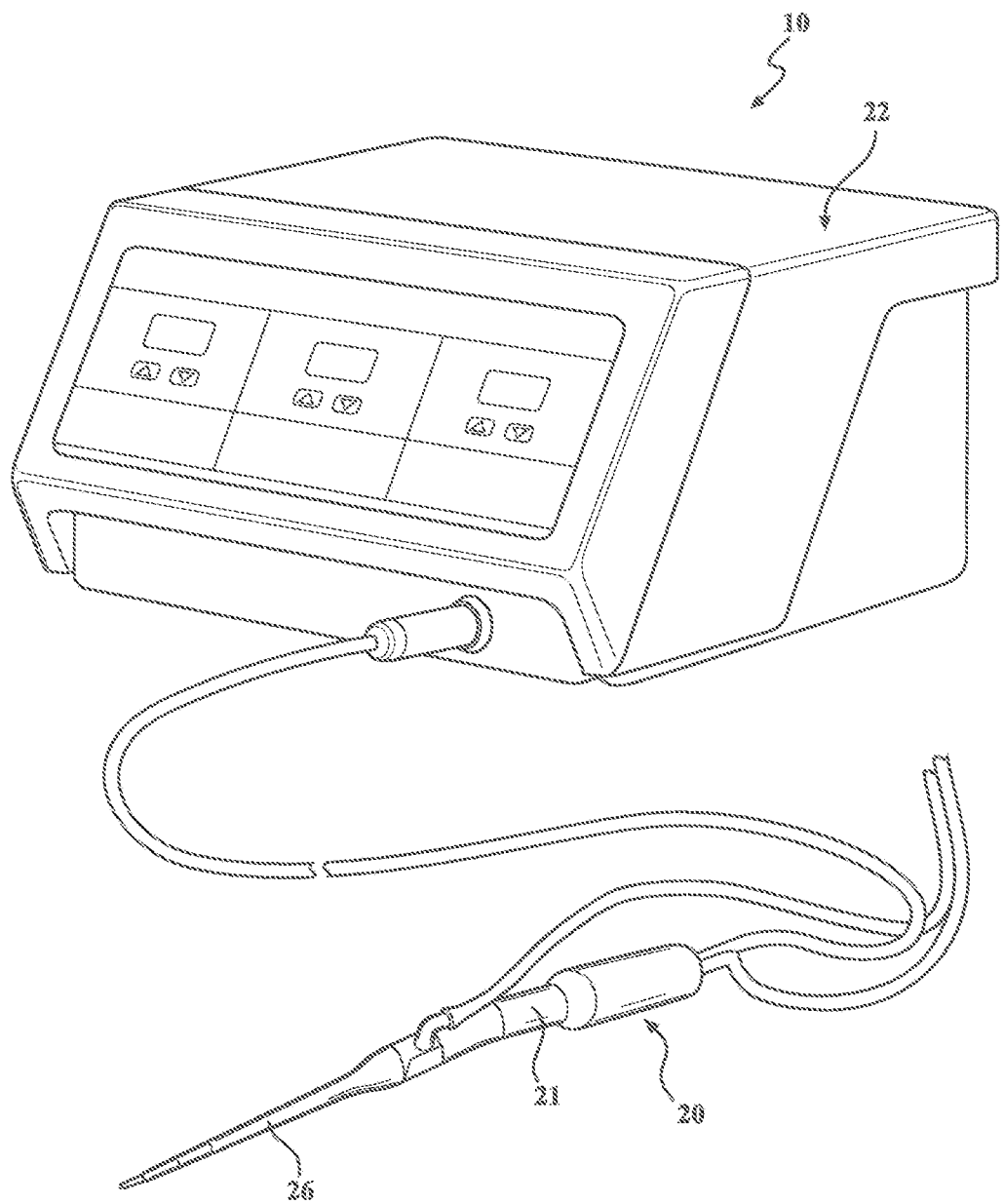
FIG. 1 is a perspective view of a console and an ultrasonic surgical tool according to one embodiment of the present invention.

As shown in FIG. 1, the system 10 includes the ultrasonic surgical tool 20 and a console 22 for controlling the ultrasonic surgical tool 20. The surgical tool 20 is connected to the console 22. Examples of the surgical tool 20, include, but are not limited to medical devices, including, but not limited to, ultrasonic aspirators, ultrasonic sealers, ultrasonic cutters, and the like.

Figure 2:
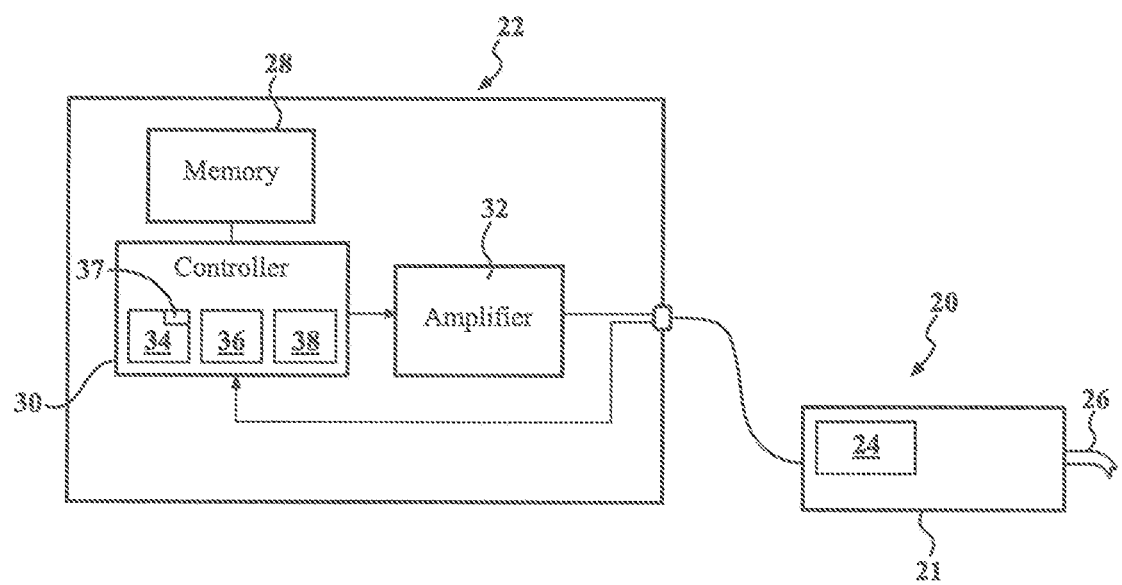
FIG. 2 is a schematic block diagram of components of the console and the surgical tool according to one embodiment of the present invention.

The surgical tool 20 includes a handpiece 21. As shown in FIG. 2, a transducer 24 is housed within the handpiece 21. The transducer 24 may comprise any suitable elements or components, such as piezoceramic elements, suitable for converting electrical energy into mechanical energy. The surgical tool 20 further includes a tip 26 that has a distal end configured to engage tissue. Examples of engagement of the tissue may include cutting and/or sealing of tissue. The tip 26 may be coupled to the transducer 24.

The surgical tool 20 may utilize a variety of interchangeable tips 26. The tip 26 may be permanently or detachably affixed to the handpiece 21. The tip 26 may have any suitable function and configuration, and may include, for example, soft tissue ablation tips and fine bone dissection tips. Examples of preferred tips 26 include, but are not limited to, Stryker® Straight™, Stryker® Barracuda®, for soft tissue and Stryker® Claw™, Stryker® Knife™, and Stryker® Payner™ for hard tissue.

In one embodiment, the console 22 includes a memory 28, a controller 30, and an amplifier 32. The memory 28 is configured to store data relevant to control of the surgical tool 20. The memory 28 may be any suitable type of memory, such as nonvolatile memory, ROM, EEPROM, RAM, flash memory, and the like. The console 22 may have any suitable firmware or software stored on the memory 28 to facilitate control of the surgical tool 20. The controller 30 is connected to the memory 28. The controller 30 may include one or more processors for executing instructions stored in the memory 28. The controller 30 is in communication with the amplifier 32 for outputting signals to the surgical tool 20. The amplifier 32 is in one embodiment, a linear amplifier.

The controller 30 may communicate with a sampling module 34, a signal generator 36, and a signal combiner 38. In FIG. 2, the sampling module 34, signal generator 36, and signal combiner 38 are part of, or integrated with, the controller 30. Alternatively, any one of, or a combination of, the sampling module 34, the signal generator 36, and the signal combiner 38 may be physically located outside of the controller 30 such that they are physically separate from the controller 30. Furthermore, in some instances, any of the sampling module 34, signal generator 36, and signal combiner 38 may be combined such that they are integrated by the same component or implemented by the same software. The sampling module 34 may be in communication with, and may include, a fast-Fourier transform (FFT) module 37.

Any of the sampling module 34, signal generator 36, FFT module 37, and signal combiner 38 may include executable instructions stored in the memory 28 on the console 22 for execution by one or more processors. The functions of the sampling module 34, signal generator 36, FFT module 37, and signal combiner 38 are described in detail below.

II. The First Drive Signal and the Harmonic Signal

The console 22 is configured to apply a first drive signal 40 to the ultrasonic surgical tool 20, and more specifically, to the transducer 24. The transducer 24 converts electrical energy of the first drive signal 40 into mechanical energy. The first drive signal 40 is outputted from the amplifier 32 in the console 22, which amplifies the first drive signal 40. The voltage of the first drive signal 40 is low voltage. For example, the voltage of the first drive signal 40 is between 0-100 VAC, and more specifically between 0-10 VAC, and even more specifically, 0-5 VAC. The amplifier 32 amplifies the voltage of the first drive signal 40 up to 1000 VAC as necessary in order to maintain a desired mechanical current. The console 22 of the surgical tool 20 may include any suitable switches or buttons to allow an operator to selectively control the first drive signal 40.

Figure 3:
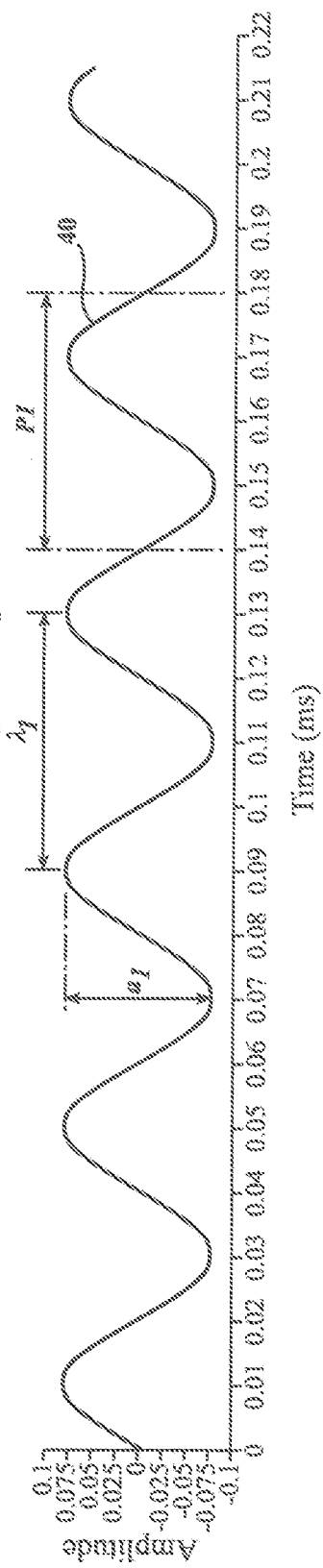
FIG. 3 is a chart illustrating a waveform of the output of a first drive signal applied by the console to the surgical tool according to one example.

FIG. 3 illustrates one example of the first drive signal 40 to one particular handpiece 21 having a sharp angle joint and micro straight tip 26 that is driven with a 25.5 kHz voltage sine wave drive signal in air at 80 mA mechanical current. Specifically, FIG. 3 is the voltage output of the first drive signal 40. The first drive signal 40 has a sinusoidal waveform. In other words, the first drive signal 40 has a waveform that exhibits a smooth repetitive oscillation. Thus, the first drive signal 40 is not a pulsed or square waveform. The sinusoidal nature of the waveform of the first drive signal 40 is important to provide ultrasonic oscillations in the tip 26. The sinusoidal waveform of the first drive signal 40 includes a frequency component, which is related to a wavelength $\lambda_1$ of the first drive signal 40. The frequency component is a fundamental (first harmonic) driving frequency 41 component. The fundamental driving frequency 41 component may also be known as a desired resonant frequency. In this example, the fundamental driving frequency 41 component is 25.5 kHz. Those skilled in the art appreciate that the fundamental driving frequency 41 component may be any suitable frequency, including frequencies in the range between 25 to 55 kHz, for example. The first drive signal 40 further includes a phase 'P1' and an amplitude '$\alpha_1$'. The console 22 is configured to generate the first drive signal 40 using the signal generator 36.

Figure 6:
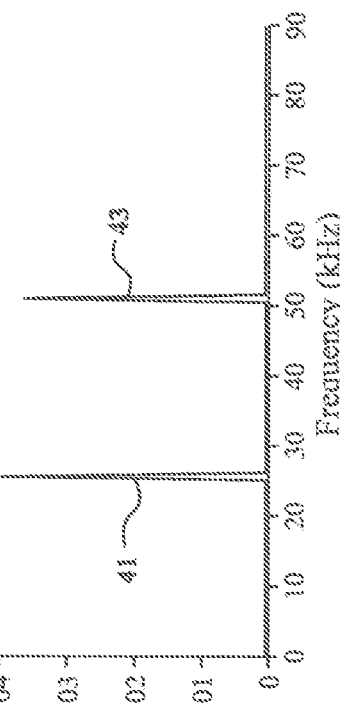
FIG. 6 is a diagram of a fast-Fourier transform of the waveform of the handpiece voltage of FIG. 5.
Figure 7:
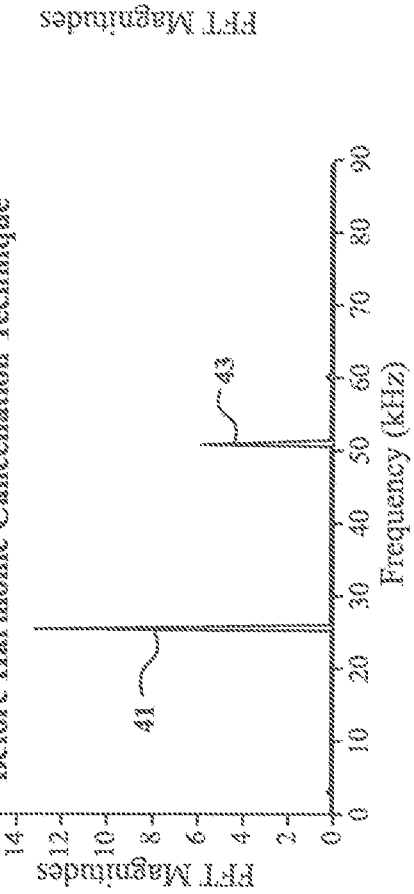
FIG. 7 is a diagram of a fast-Fourier transform of the waveform of the handpiece current of FIG. 5.

The first drive signal 40 includes several characteristics. The characteristics of the first drive signal 40 are generally related to the waveform of the first drive signal 40. Any characteristic of the first drive signal 40 may be a time-domain or frequency-domain based characteristic. For example, with respect to the time-domain as shown in FIG. 3, the characteristic of the first drive signal 40 may include at least one of the wavelength $\lambda_1$, the phase 'P1', and the amplitude '$\alpha_1$'. With respect to the frequency-domain, as shown in FIGS. 6 and 7 described below, for example, the characteristic of the first drive signal 40 may include at least one of a frequency, a magnitude, and a phase the first drive signal 40. For example, the frequency is the fundamental driving frequency 41 component. Characteristics of the first drive signal 40 may be predetermined or known. Alternatively, characteristics of the first drive signal 40 may be measured. For example, the characteristic of the first drive signal 40 may be derived from current or voltage readings relating to application of the first drive signal 40, as will be described below. Those skilled in the art appreciate that any characteristic of the first drive signal 40 may be derived from the time-domain and frequency-domain parameters, individually or in combination.

Figure 4:
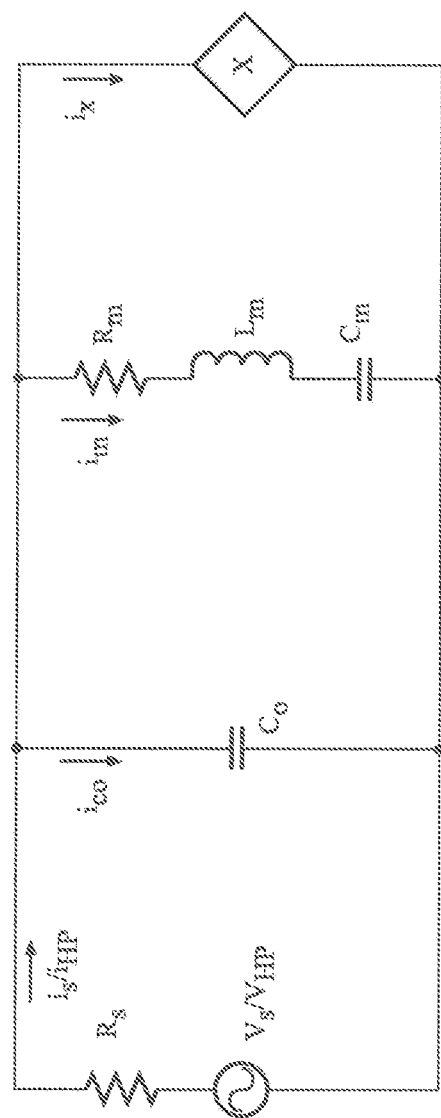
FIG. 4 illustrates an example of an electromechanical circuit model of the combination of a handpiece and a tip of the surgical tool according to one example.

FIG. 4 illustrates an example of an electromechanical circuit model of the combination of the handpiece 21 and tip 26. In FIG. 4, $V_s$ is the output drive voltage (voltage source) from the console 22. Hereinafter, the output drive voltage is referred to as a handpiece voltage, $V_{HP}$. In FIG. 4, $R_s$ is the series resistance of the console. The current through R is a source current, $i_s$, which is hereinafter referred to as the handpiece current, $i_{HP}$. The handpiece current $i_{HP}$ may be determined by an impedance of the handpiece 21. This impedance may be derived from one or more features of the handpiece 21. For example, the impedance results from loading of the tip 26, acoustical properties of the handpiece 21, acoustical properties of the tissue being resected, properties of the transducer 24, vibration of the handpiece 21, and the like.

As shown in FIG. 4, the static handpiece capacitance is $C_o$ and the current through the static capacitance $C_o$ is $i_{co}$. A vibrating resonant mode is represented by the series $R_m$, $L_m$, and $C_m$, where $i_m$ represents a desired mechanical current. The desired mechanical current $i_m$ is induced by the strain on the handpiece 21. Vibrational motion of the tip 26 is directly related to the desired mechanical current $i_m$. As such, the displacement of the tip 26 vibration increases as the mechanical current $i_m$ increases. The tip 26 operates at resonance when the desired mechanical current $i_m$ is in phase with the handpiece voltage $V_{HP}$.

The model in FIG. 4 is based on a standard Butterworth-VanDyke model, but is improved by capturing generic component X and its effects on the model. Generic component X is a theoretical component that creates a harmonic signal 44 resulting from application of the first drive signal 40 to the surgical tool 20, and more specifically, the handpiece 21 and tip 26 combination. The harmonic signal 44 may include any higher order harmonic, such as a second, third, or fourth order harmonic of the fundamental drive frequency 41 component, or any combination thereof. The harmonic signal 44 is generally an unwanted signal because the harmonic signal 44 is responsible for harmonic distortion. Hereinafter, the frequency of the harmonic signal 44 is referred to as the harmonic frequency 43 component. The harmonic signal 44 may be naturally occurring based on the specific combination of the handpiece 21 and tip 26. In some instances, the harmonic signal 44 does not appear until a minimum threshold displacement of the tip 26 is achieved. Such behavior is considered non-linear behavior. The current through generic component X, $i_x$, represents an undesired mechanical current. In some versions of the model, the generic component X can be a vibration current source that is dependent on, or related to, the desired mechanical current, $i_m$.

Figure 5:
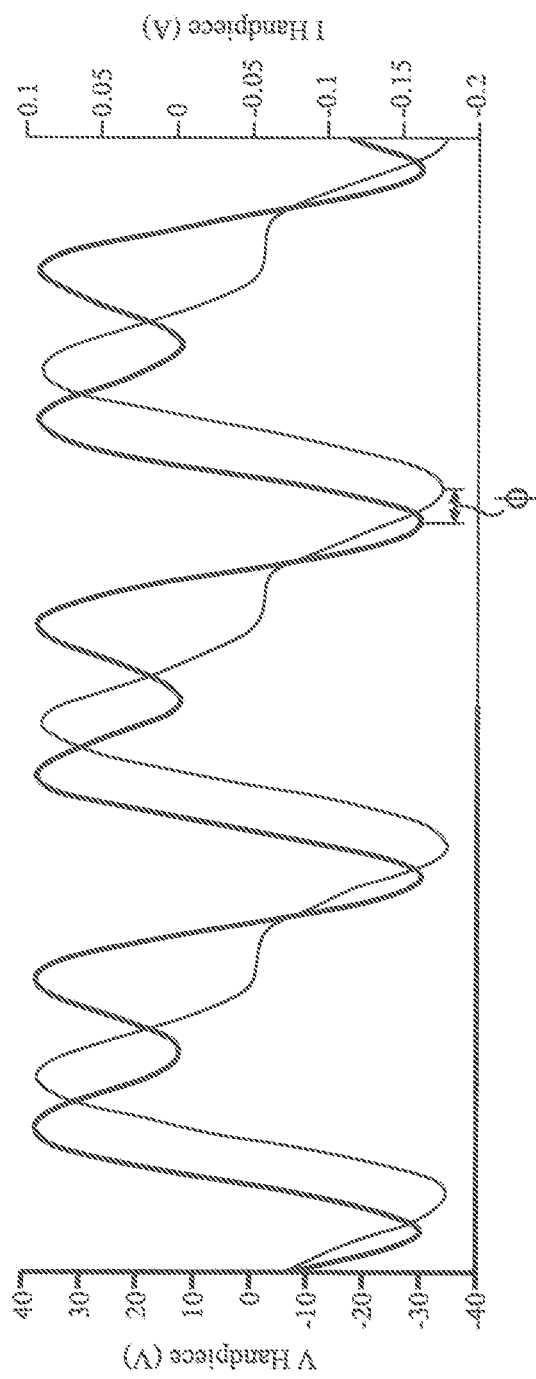
FIG. 5 is a chart of waveforms of a voltage and current of the handpiece resulting from the first drive signal of FIG. 3 before application of the harmonic cancellation method.

FIG. 5 illustrates the waveforms of the handpiece current $i_{HP}$ and handpiece voltage $V_{HP}$ and an exemplary effect of the harmonic signal 44 on the handpiece current $i_{HP}$ and voltage $V_{HP}$ waveforms before application of the harmonic cancellation method 12 described herein. Since the first drive signal 40 is sinusoidal and has a signal frequency component, the handpiece current $i_{HP}$ and handpiece voltage $V_{HP}$ are consequently sinusoidal and have a signal frequency component. In this case, the waveform of the handpiece current $i_{HP}$ exhibits a variable phase shift $\Phi$ relative to the handpiece voltage $V_{HP}$ because the fundamental driving frequency 41 component is accompanied by the harmonic frequency 43 component. Since the handpiece current $i_{HP}$ and handpiece voltage $V_{HP}$ exhibit multiple frequency components, the waveforms are not purely sinusoidal. The handpiece current $i_{HP}$ and handpiece voltage $V_{HP}$ differ depending upon, among other things, the specific tip 26 being utilized.

FIGS. 6 and 7 illustrate the respective fast-Fourier analyses for each of the waveforms for the handpiece voltage $V_{HP}$ and handpiece current $i_{HP}$ from FIG. 5. The analysis identifies the frequency (or frequencies) most responsible for the observed distortion shown in FIG. 5. In this example, FFT analysis reveals that the fundamental driving frequency 41 component (i.e., 25.5 kHz) is accompanied by the additional harmonic frequency 43 component from the harmonic signal 44 (e.g., 51 kHz). The harmonic signal 44 is responsible for the resulting harmonic distortion. For the handpiece voltage $V_{HP}$, the harmonic frequency 43 component exhibits a magnitude of over 40% of the magnitude of the fundamental drive frequency 41 component. For the handpiece current $i_{HP}$, the harmonic frequency 43 component has a magnitude of over 90% of the magnitude of the fundamental driving frequency 41 component. It should be appreciated FIGS. 6 and 7 illustrate one example of the harmonic frequency 43 component. As such, the harmonic frequency 43 component may be different from and may have a magnitude different than the harmonic frequency in FIGS. 6 and 7.

Further analysis of the data reveals that the phase angle θ between the harmonic signal 44 in the waveforms for the handpiece voltage $V_{HP}$ and handpiece current $i_{HP}$ is 103°. This phase angle θ is larger than 90°, which gives a negative power factor indicating that the handpiece 21 and tip 26, in combination, produce power at 51 kHz (instead of the console producing power at 51 kHz). In this case, the 25.5 kHz vibration induces a 51 kHz vibration due to the non-linear vibrational behavior of the handpiece 21 and tip 26 combination. The 51 kHz vibration moves the piezoelectric elements in the transducer 24 thereby converting some of the mechanical energy to electrical energy at 51 kHz, the harmonic frequency 43 component.

Figure 8:
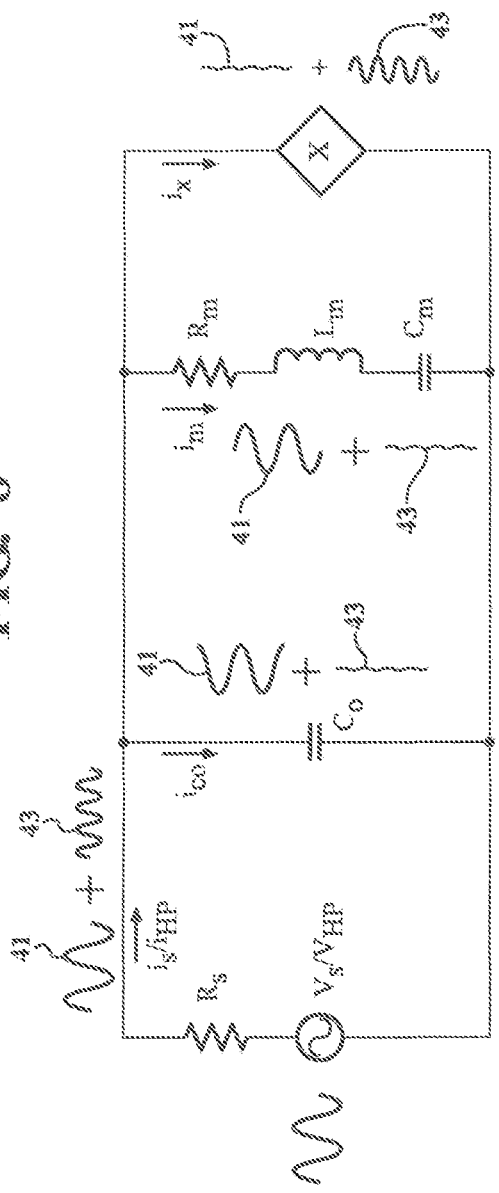
FIG. 8 is the electromechanical circuit model of FIG. 4 further illustrating respective contributions of a fundamental driving frequency and a harmonic frequency of a harmonic signal resulting from application of the first drive signal to the current in each branch of the circuit.

FIG. 8 illustrates respective contributions of the fundamental driving frequency 41 component and the harmonic frequency 43 component to the current in each branch of the circuit from FIG. 4. The contributions are based on an assumption of a low value of $R_m$ with respect to the impedance of $C_o$ and an assumption that the series impedance of $R_m$, $L_m$, $C_m$ has relatively high impedance at the harmonic frequency 43 component. In FIG. 8, the fundamental driving frequency 41 component and the harmonic frequency 43 component each contribute significantly to the handpiece current $i_{HP}$. The fundamental driving frequency 41 component contributes significantly to the current $i_{co}$ through the static capacitance $C_o$ and the desired mechanical current $i_m$. To the contrary, the harmonic frequency 43 component has virtually no contribution to the current $i_{co}$ through the static capacitance and the desired mechanical current $i_m$. Yet, for the unwanted mechanical current $i_x$, the fundamental driving frequency 41 component has virtually no contribution whereas the harmonic frequency 43 component has significant contribution. As such, based on this model, the harmonic signal 44 present in the handpiece current $i_{HP}$ relates directly to presence of the undesired mechanical current $i_x$ through generic component X.

III. Second Drive Signal and Reduction of Harmonic Signal

Figure 9:
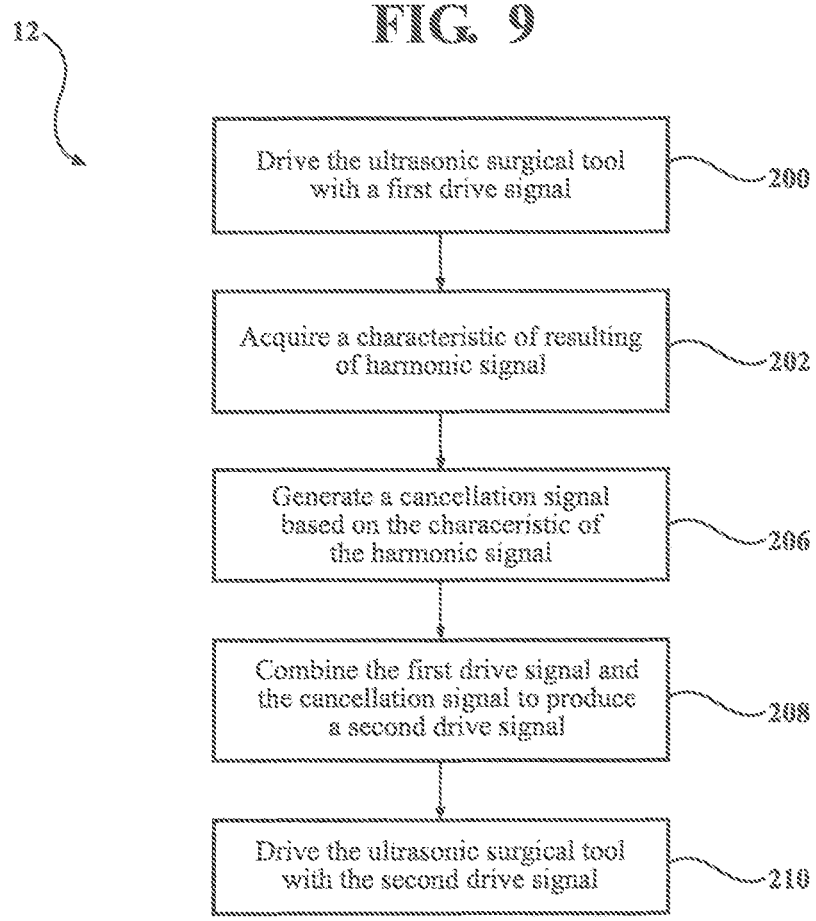
FIG. 9 is a flowchart of a method of controlling the ultrasonic surgical tool to reduce presence of the harmonic signal resulting from driving the ultrasonic surgical tool with the first drive signal of FIG. 3 according to one embodiment of the present invention.

The system 10 and method 12 reduce presence of the aforementioned harmonic signal 44. As shown in FIG. 9, the method 12 may include applying the first drive signal 40 to the ultrasonic tool 20 at step 200. At step 202, at least one characteristic of the harmonic signal 44 resulting from application of the first drive signal 40 to the ultrasonic surgical tool 20 is acquired. A cancellation signal 70 is generated based on the acquired characteristic of the harmonic signal 44 at step 206. At step 208, the console 22 combines the first drive signal 40 and the cancellation signal 70 to produce a second drive signal 80, wherein the second drive signal 80 is sinusoidal. At step 210, the console 22 applies the second drive signal 80 to the ultrasonic surgical tool 20. The presence of the harmonic signal 44 resulting from application of the second drive signal 50 is reduced relative to presence of the harmonic signal 44 resulting from application of the first drive signal 40. The specific steps of this method 12 are described in detail below.

The console 22 performs step 202 to acquire the characteristic of the harmonic signal 44. The characteristic of the harmonic signal 44 may be a time-domain or frequency-domain based characteristic. For example, with respect to the time-domain, the characteristic of the harmonic signal 44 may include (with reference to FIG. 13) at least one of a wavelength $\lambda_2$ a phase 'P2', and an amplitude '$\alpha_2$'. With respect to the frequency-domain, as shown in FIGS. 6 and 7 described below, for example, the characteristic of the harmonic signal 44 may include at least one of a frequency, a magnitude, and a phase the harmonic signal 44. For example, the frequency of the harmonic signal 44 is the harmonic frequency 43 component, and more specifically, the second harmonic frequency (e.g., 51 kHz). Those skilled in the art appreciate that any characteristic of the harmonic signal 44 may be acquired from the time-domain and frequency-domain, individually or in combination.

As described, the characteristics of the first drive signal 40 may be predetermined or known. Thus, the characteristic of the first drive signal 40 and the characteristic of the harmonic signal 44 may be determined at different moments. Alternatively or additionally, if the characteristic of the first drive signal 40 is unknown, the console 22 may perform step 202 to further acquire the characteristic of the first drive signal 40. In other words, the characteristic of the first drive signal 40 and the characteristic of the harmonic signal 44 may be determined at the same moment or at different times.

In one embodiment, the console 22 acquires the characteristic of the harmonic signal 44, in part, by generating current and voltage samples relating to application of the first drive signal 40. More specifically, the voltage samples are based on the handpiece voltage $V_{HP}$ and the current samples are based on the handpiece current $i_{HP}$. The characteristics of the harmonic signal 44 are related to the waveform of the harmonic signal 44. Therefore, the characteristics of the harmonic signal 44 are present in and may be extracted from the current and voltage samples.

In one example, the console 22 acquires the characteristic of the harmonic signal 44 by measuring or starting with the known static capacitance value, $C_o$. The magnitude and phase of both the voltage and current for the fundamental frequency 41 component of the first drive signal 40 are predetermined or known and may be accessed from the memory 28. Knowing this information, the console 22 drives the handpiece 21 and tip 26 with the first drive signal 40, as configured, at relatively low vibration levels at the fundamental frequency 41 component (e.g., 25.5 kHz). The console 22 may maintain driving the handpiece 21 and tip 26 at the fundamental frequency 41 component by using a tracking algorithm to monitor resonance. The tracking algorithm is implemented by the controller 30. The controller 30 continuously measures and/or calculates resonance of the handpiece 21 and tip 26 as they vibrate. The tracking algorithm is configured to make appropriate adjustments to achieve the designed resonance if the measured resonance deviates from the desired resonance. The tracking algorithm may be implemented continuously during operation of the surgical tool 20. Those skilled in the art appreciate that any suitable tracking algorithm may be implemented.

The console 22 uses the sampling module 34 to acquire the current and voltage samples resulting from application of the first drive signal 40. The console 22 acquires the current and voltage samples by sampling the handpiece current $i_{HP}$ and handpiece voltage $V_{HP}$, such as shown in FIG. 5 above, for example. Alternatively, the console 22 may monitor and/or sample the impedance of the handpiece 21 and tip 26 to derive the current and voltage samples. The console 22 is configured to convert the current and voltage samples for further analysis using including analog-to-digital conversion devices, and the like. Those skilled in the art understand that the console 22 need not generate waveforms, such as in FIG. 5, to sample or analyze characteristics of the first drive signal 40 and/or harmonic signal 44. Instead, the samples may be generated and analyzed based on non-visual data, such as binary values. The console 22 may acquire the samples during or after application of the first drive signal 40 to the surgical tool 20. The acquired samples may be stored in the memory 28 such that the controller 30 may accesses the samples at any suitable time after acquisition of the samples.

The console 22 analyzes the samples to acquire the characteristic of the harmonic signal 44. By acquiring the characteristic of the harmonic signal 44, the console 22 can measure the distortion (e.g. at the second harmonic frequency 43) in both the handpiece current $i_{HP}$ and handpiece voltage $V_{HP}$. In one example, the console 22 uses FFT analysis techniques to acquire the characteristic of the harmonic signal 44. Here, the console 22, and more specifically the FFT module 37, executes the FFT of the current and voltage samples. The console 22 may acquire and process the current and voltage samples real-time during application of any drive signal.

Figure 10:
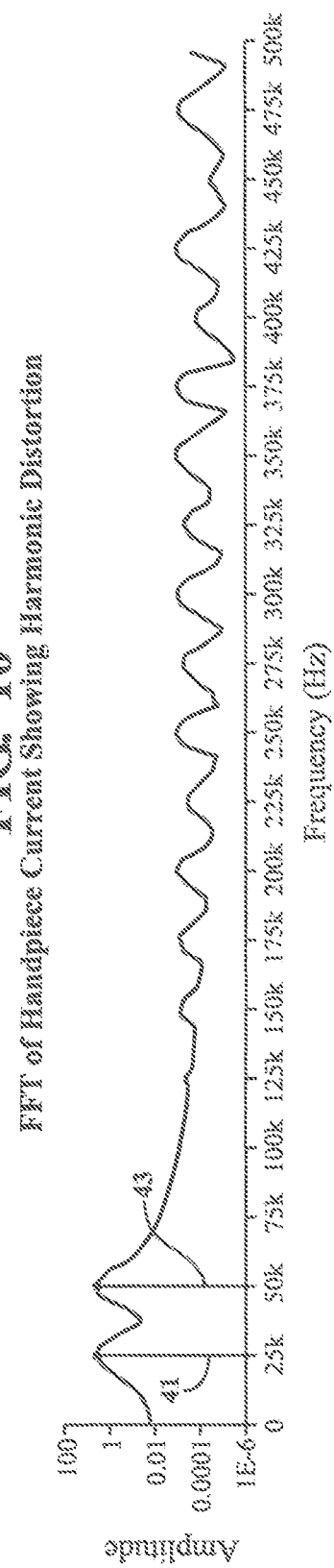
FIG. 10 is a chart of the waveform of the fast-Fourier transform of the handpiece current showing the fundamental and harmonic frequency components.

FIG. 10 illustrates an example of the FFT of sampled handpiece current $i_{HP}$ showing the 25.5 kHz and 51 kHz frequency components exhibiting significant amplitude in comparison to the remainder of the spectrum. If the console 22 determines that the measured distortion based on the samples is appreciably low, the console 22 may continue to increase the mechanical current, $i_m$, until an unacceptable harmonic vibration is achieved. Here, the console 22 increases the mechanical current, $i_m$, until the amplitude of the harmonic frequency 43 component (second harmonic) is nearly as great as the amplitude of the fundamental driving frequency 41 component, i.e., 25.5 kHz.

The characteristic of the harmonic signal 44 may additionally be understood based on FIGS. 6 and 7, described above, which illustrate charts representing the result of performing the FFT in the example described. For simplicity, the contents of FIGS. 6 and 7 are not repeated. Those skilled in the art understand that the FFT may yield data indicative of the transform, and therefore, charts, such as those in FIGS. 6, 7 and 10 need not be generated to acquire the characteristic of the harmonic signal 44. Accordingly, in certain embodiments, the FFT of the current and voltage waveforms is performed in effort to actively generate the second drive signal 80, and therefore, the FFT is not used merely for diagnostic purposes.

To determine characteristics of the harmonic signal 44, the console 22 may further compare characteristics of the first drive signal 40 and characteristics of the harmonic signal 44. In one example, the console 22 determines the difference between the phase P1 of the first drive signal 40 and the phase P2 of the harmonic signal 44. Alternatively, the console 22 determines the difference between the phase of the handpiece voltage $V_{HP}$ at the fundamental frequency 41 component and the phase of the handpiece current $i_{HP}$ at the harmonic frequency 43 component. Said differently, the console 22 determines the phase of the handpiece current $i_{HP}$ at the second harmonic frequency with respect to the handpiece voltage $V_{HP}$ at the first harmonic frequency. The phase of the handpiece current $i_{HP}$ at the second harmonic frequency with respect to the handpiece voltage $V_{HP}$ at the first harmonic frequency is also known as the phase angle.

Figure 11:
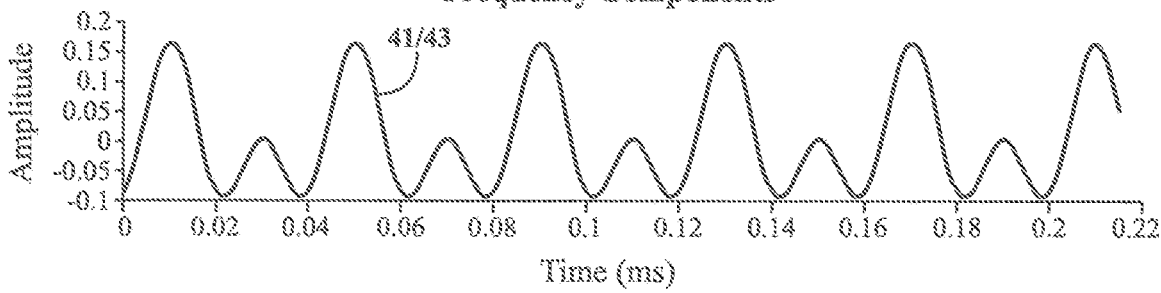
FIG. 11 is a chart of the waveform of the handpiece current showing the fundamental and harmonic frequency components.

To accomplish this, the console 22 separates the fundamental frequency 41 component from the harmonic frequency 43 component for at least one of the handpiece voltage $V_{HP}$ and handpiece current $i_{HP}$. For example, FIG. 11 illustrates the sampled handpiece current $i_{HP}$, which is similar to the handpiece current $i_{HP}$ illustrated in FIG. 5. The waveform of the sampled handpiece current $i_{HP}$ includes two frequency components, i.e., the fundamental frequency 41 component and the harmonic frequency 43 component.

Figure 12:
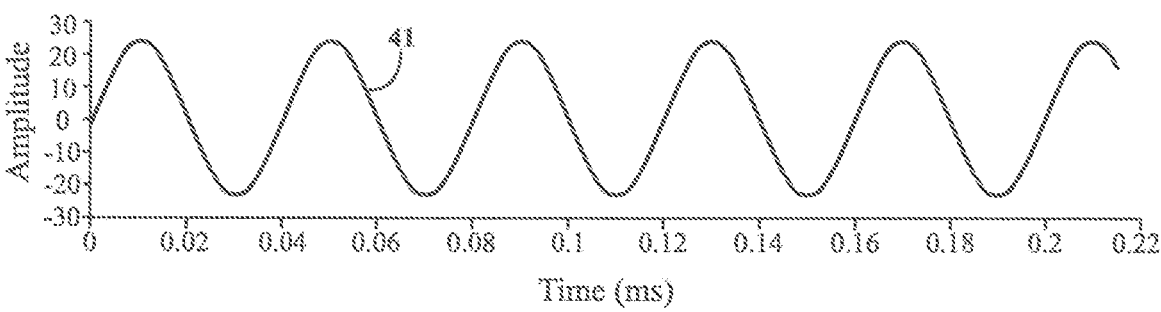
FIG. 12 is a chart of the waveform of the fundamental frequency component of the handpiece current of FIG. 11 in isolation.

FIG. 12 illustrates the waveform of the fundamental frequency 41 component extracted from the handpiece voltage $V_{HP}$. Notably, in this example, the waveform in FIG. 12 is identical to the source waveform of the first drive signal 40 in FIG. 3. That is, the waveform including the isolated fundamental frequency 41 component is equivalent to the source waveform of the first drive signal 40 prior to introduction of the harmonic signal 44 resulting from application of the first drive signal 40.

Figure 13:
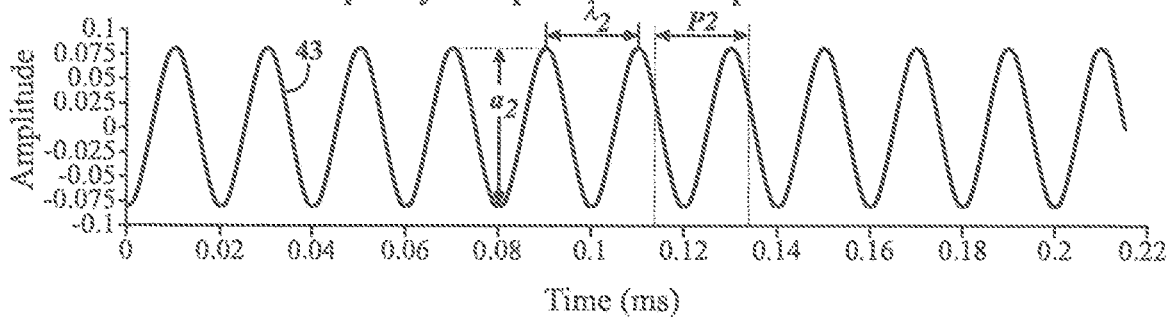
FIG. 13 is a chart of the waveform of the harmonic frequency component of the handpiece current of FIG. 11 in isolation.

FIG. 13 illustrates the isolated waveform of the harmonic frequency 43 component extracted from the handpiece current $i_{HP}$ in FIG. 11. Thus, FIG. 3 illustrates the harmonic signal 44 isolated from the resulting application of the first drive signal 40. As shown, the harmonic signal 44 has a sinusoidal waveform including a frequency component, which is related to the wavelength $\lambda_2$ of the harmonic signal 44. The harmonic signal 44 also includes the phase "P2" and amplitude "$\alpha_2$".

In one embodiment, the console 22 determines the difference between the phase of the handpiece voltage $V_{HP}$ at the fundamental frequency 41 component and the phase of the handpiece current $i_{HP}$ at the harmonic frequency 43 by calculating the phase angle. Using the specific frequencies, phases, and amplitudes of the handpiece voltage $V_{HP}$ and the handpiece current $i_{HP}$ in this example, the console 22 computes the phase angle using the following equation:

$$i_{HP}=0.08\cdot\sin(2\pi\cdot 25.5 \text{ kHz}\cdot t+0)+0.083\cdot\sin(2\pi\cdot 51 \text{ kHz}\cdot t-90) \qquad [1]$$

Here, the console 22 determines that the harmonic frequency 44 (51.5 kHz) of the handpiece current $i_{HP}$ is −90° out of phase to the handpiece voltage $V_{HP}$ at the fundamental frequency 41 component (25.5 kHz). Determining that the phase angle is −90° out of phase allows the console 22 to calibrate the cancellation signal 70. Mainly, the phase of the cancellation signal 70 is shifted 180 degrees relative to the phase of the harmonic signal 44 to mathematically cancel the amplitude of the harmonic signal 44. The cancellation signal 70 is referenced to the first drive signal 40. The current of the cancellation signal 70 is naturally in-phase with the voltage of the cancellation signal 70. The waveform of the discovered harmonic current is shifted by 90 degrees from the first drive signal 40. For the cancellation signal 70 to cancel out the harmonic signal 44, the cancellation signal 70 is shifted by 90 degrees in the opposition direction (−90) with respect to the first drive signal 40. As a result, the phase of the cancellation signal 70 is shifted 180 degrees relative to the phase of the harmonic signal 44.

At step 206, the method 12 includes generating the cancellation signal 70 with the console 22 based on the characteristic of the harmonic signal 44. The cancellation signal 70 is configured to reduce the presence of the harmonic signal 44 thereby minimizing the effects of the harmonic signal 44. In one embodiment, the cancellation signal 70 is designed such that it has the greatest effect on reducing the presence of the harmonic signal 44. In effect, the cancellation signal 70 is based on one or more characteristic of the undesired mechanical current $i_x$. Accordingly, the cancellation signal 70 minimizes the presence of the harmonic signal 44 in the undesired mechanical current $i_x$. Said differently, in the example described herein, the cancellation signal 70 minimizes the undesired mechanical current $i_x$ at the second harmonic frequency 43 component thereby minimizing the harmonic distortion in the handpiece current $i_{HP}$. The console 22 is configured to generate the cancellation signal 70 using the signal generator 36. Data relating to the generated cancellation signal 70 may be stored in the memory 28.

FIG. 14 illustrates the one example of the waveform of the cancellation signal 70. As shown, the cancellation signal 70 has a sinusoidal waveform including a frequency component, which is related to a wavelength $\lambda_3$ of the cancellation signal 70. The cancellation signal 70 also includes a phase "P3" and an amplitude "$\alpha_3$".

In one embodiment, the console 22 generates the cancellation signal 70 based on the frequency of the harmonic signal 44. For example, the frequency of the cancellation signal 70 may be designed to minimize the harmonic signal 44. More specifically, the console 22 generates the cancellation signal 70 such that the frequency of the cancellation signal 70 is similar to the frequency of the harmonic signal 44. As such, the wavelength $\lambda_3$ of the cancellation signal 70 in FIG. 14 is the same as the wavelength $\lambda_2$ of the harmonic signal 44 in FIG. 13. More specifically, in this example, the frequency of the cancellation signal 70 is set at 51 kHz, which is the determined frequency of the harmonic signal 44. By having the same frequency as the harmonic signal 44, the cancellation signal 70 directly targets the harmonic frequency 43 component to reduce its effects without affecting the fundamental driving frequency 41 component or otherwise introducing other unwanted frequencies. Those skilled in the art appreciate that there may be instances when the frequency of the cancellation signal 70 is similar to, but not exactly equal to, the harmonic frequency 43 component. For example, the frequency of the cancellation signal 70 may be a few hundred Hertz greater than or less than the harmonic frequency 43 to account for residual effects of the harmonic signal 44. In another example, the frequency of the cancellation signal 70 may be a 1 kHz greater than or less than the harmonic frequency 43.

The cancellation signal 70 may be further designed such that the phase P3 of the cancellation signal 70 is shifted relative to the phase P2 of the harmonic signal 44. In one embodiment, the phase P3 of the cancellation signal 70 be designed to minimize the harmonic signal 44. In one example, the phase P3 of the cancellation signal 70 is shifted 180 degrees relative to the phase P2 of the harmonic signal 44. As such, the phase P3 of the cancellation signal 70 in FIG. 14 is shifted one-half period relative to the phase P2 of the harmonic signal 44 in FIG. 13. By having the phase P3 shifted 180 degrees relative to the phase P2 of the harmonic signal 44, the cancellation signal 70 maximizes its canceling effect of the harmonic signal 44 because the amplitude $\alpha_3$ of the cancellation signal 70 is opposite of the amplitude $\alpha_2$ of the harmonic signal 44, as shown in FIG. 14. Those skilled in the art appreciate that there may be instances when the phase P3 of the cancellation signal 70 is shifted relative to the phase P2 of the harmonic signal 44 by degrees other than 180 degrees. For example, the phase P3 of the cancellation signal 70 may be shifted by any odd, positive or negative, multiple of 180 degrees, such as 540 degrees, −180 degrees, and the like.

The cancellation signal 70 may further be designed such that the amplitude $\alpha_3$ of the cancellation signal 70 is adjusted relative to the amplitude $\alpha_2$ of the harmonic signal 44. In one embodiment, as shown in FIG. 14, the amplitude $\alpha_3$ of the cancellation signal 70 is equal to the amplitude $\alpha_2$ of the harmonic signal 44. By having the amplitude as of the cancellation signal 70 equal to the amplitude $\alpha_2$ of the harmonic signal 44, the cancellation signal 70 maximizes its cancelling effect of the harmonic signal 44. That is, the amplitude $\alpha_3$ of the cancellation signal 70 is equal to and opposite (based on the phase shift) of the amplitude $\alpha_2$ of the harmonic signal 44, as shown in FIG. 14.

Alternatively, if desired, the cancellation signal 70 may further be designed such that the amplitude $\alpha_3$ of the cancellation signal 70 is greater than or less than the amplitude $\alpha_2$ of the harmonic signal 44. For example, in one instance, the amplitude $\alpha_3$ of the cancellation signal 70 is twice the amplitude $\alpha_2$ of the harmonic signal 44. Those skilled in the art appreciate that there may be instances when the amplitude $\alpha_3$ of the cancellation signal 70 may be set relative to the amplitude $\alpha_2$ of the harmonic signal 44 according to various other levels not specifically described herein. In one embodiment, the phase $\alpha_3$ of the cancellation signal 70 may be designed to minimize the harmonic signal 44.

In other embodiments, the amplitude as of the cancellation signal 70 is determined based on an amplitude adjusting algorithm designed to monitor the effects of amplitude changes in the cancellation signal 70 on the harmonic signal 44. For example, the amplitude adjusting algorithm may start with relatively low amplitude $\alpha_3$ and increase the amplitude $\alpha_3$ until the harmonic frequency 43 component is minimized. The console 22 may monitor the effects on the harmonic frequency 43 component using a feedback loop.

Those skilled in the art appreciate that the console 22 may generate the cancellation signal 70 based on at least one of, or a combination of, any characteristics of the harmonic signal 44. For example, the cancellation signal 70 may be generated based on the frequency and amplitude $\alpha_2$ of the harmonic signal 44, but not the phase P2 of the harmonic signal 44. Alternatively, the cancellation signal 70 may be generated based on the frequency and phase P2 of the harmonic signal 44, but not the amplitude $\alpha_2$ of the harmonic signal 44. In such instances where some characteristics of the harmonic signal 44 are not considered when designing the cancellation signal 70, the cancellation signal 70 may be generated based on alternative or default frequencies, phases, or amplitudes, for example.

At step 208, the console 22 combines the first drive signal 40 and the cancellation signal 70 to produce a second drive signal 80. In other words, the console 22 produces the second drive signal 80 by combining the cancellation signal 70 and the original or source first drive signal 40 (without the resulting harmonic signal 44). The console 22 adds these two signals using the signal combiner 38. The console 22 may access information about the first drive signal 40 and cancellation signal 70 from the memory 28.

FIG. 15 illustrates the output drive voltage of the second drive signal 80 for the example described herein. Like the first drive signal 40, the second drive signal 80 is sinusoidal to facilitate appropriate ultrasonic operation of the surgical tool 20.

The cancellation signal 70 is effectively combined with the handpiece voltage $V_{HP}$. As such, the output drive voltage of the second drive signal 80 may be understood as a modified handpiece voltage $V_{HP'}$, that is, modified relative to the original handpiece voltage $V_{HP}$ of the first drive signal 40. The second drive signal 80 in FIG. 15 is based on the combination of the 25.5 kHz first drive signal 40 (FIG. 12) and the 51 kHz cancellation signal 70 (FIG. 14). As such, the voltage output of the second drive signal 80 contains both the 25.5 kHz drive signal and the 51 kHz cancellation signal. In other words, the cancellation signal 70 provides a second frequency component 77 to accommodate the fundamental frequency 41 component of the main drive voltage $V_{HP}$. This second frequency component 77 is at the second harmonic frequency 43 component with a phase shift that is 180° out of phase compared to the harmonic frequency 43 component thereby effectively minimizing the harmonic frequency 43 component.

The console 22, and more specifically, the signal combiner 38, is configured to combine the first drive signal 40 and the cancellation signal 70 using mathematical operations. For the example described herein, the signal combiner 38 combines the signals using the following equation [2]:

$$v_{HP'} = A \cdot \sin(2\pi \cdot f_1 \cdot t) + B_{canceling\_amp} \cdot \sin(2\pi \cdot f_2 \cdot t + \theta_{canceling\_phase}) \quad [2]$$

More specifically, inputting the respective frequencies, phases, and amplitudes of the first drive signal 40 and the cancellation signal 70, equation [2] is expressed as follows:

$$V_{HP'} = 25 \cdot \sin(2 \cdot 25.5 \text{ kHz} \cdot t) + 8 \cdot \sin(2\pi \cdot 51 \text{ kHz} \cdot t + 90) \quad [2]$$

At step 210, the console 22 applies the second drive signal 80 to the ultrasonic surgical tool 20. Similar to the first drive signal 40, the console 22 is configured to apply the second drive signal 40 to the ultrasonic surgical tool 20, and more specifically, to the transducer 24. That is, the amplifier 32 amplifies the voltage of the second drive signal 80 and the transducer 24 converts electrical energy of the second drive signal 80 into mechanical energy.

By incorporation of the cancellation signal 70, the second drive signal 80 is specifically designed to exhibit a reduction in the harmonic signal 44. The second drive signal 80 drives the transducer 24 to create a force that opposes the undesired vibrational motion. This opposing force effectively cancels the undesired vibration. In effect, the presence of the harmonic signal 44 resulting from application of the second drive signal 80 is reduced relative to presence of the harmonic signal 44 resulting from application of the first drive signal 40. More specifically, the presence of the harmonic signal 44 in the undesired mechanical current $i_x$ after application of the second drive signal 80 is reduced. Said differently, in the example described herein, the undesired mechanical current $i_x$ at the second harmonic frequency 43 component is minimized after application of the second drive signal 80 thereby minimizing the harmonic distortion in the handpiece current $i_{HP}$.

In some embodiments, the console 22 is configured to generate the cancellation signal 70 repeatedly during operation of the surgical tool 20. For example, the console 22 may output "n" drive signals (e.g., first, second, third drive signals, etc.) and acquire characteristics of the harmonic signals (if present) resulting from application of each "nth" drive signal. The console 22 may track the harmonic distortion and provide "n" cancellation signals throughout the use of the tip 26 or throughout the surgical procedure. In such instances, each "nth" drive signal, each "nth" cancellation signal and each resulting harmonic signal may be different from one another. In some embodiments, the console 22 continues this process until the console 22 determines that the harmonic signal 44 is at an appropriate level. For example, the console 22 may continue this process until the console 22 determines that the harmonic signal 44 is below a predetermined threshold (e.g. magnitude of harmonic frequency 43 component being less than 5% of magnitude of fundamental frequency 41 component) or until the harmonic signal 44 is eliminated.

The console 22 may use any suitable method to measure and track the harmonic signal 44 levels in effort to generate the cancellation signal 70 or each "nth" cancellation signal. In one example, the console 22 calculates the harmonic frequency 43 component in the handpiece current $i_{HP}$ using the known value for $C_o$. When minimized close to zero, the harmonic frequency 43 component in the current $i_{co}$ through $C_o$ represents the remaining unwanted motional current $i_x$.

FIG. 15 illustrates the waveforms of the modified handpiece current $i_{HP'}$ and handpiece voltage $V_{HP'}$ after application of the harmonic cancellation method 12. In comparison to the waveforms in FIG. 5, the effects of the harmonic signal 44 on the waveforms in FIG. 15 are drastically minimized. After application of the second drive signal 80, the waveform of the handpiece current $i_{HP'}$ exhibits minimal phase shift φ relative to the handpiece voltage $V_{HP'}$ because the fundamental driving frequency 41 component is significantly unaffected by the harmonic frequency 43 component. Further, since the handpiece current $i_{HP'}$ and handpiece voltage $V_{HP'}$ exhibit predominately only one frequency component, i.e., the fundamental driving frequency 41 component, the waveforms are substantially sinusoidal.

Figure 16:
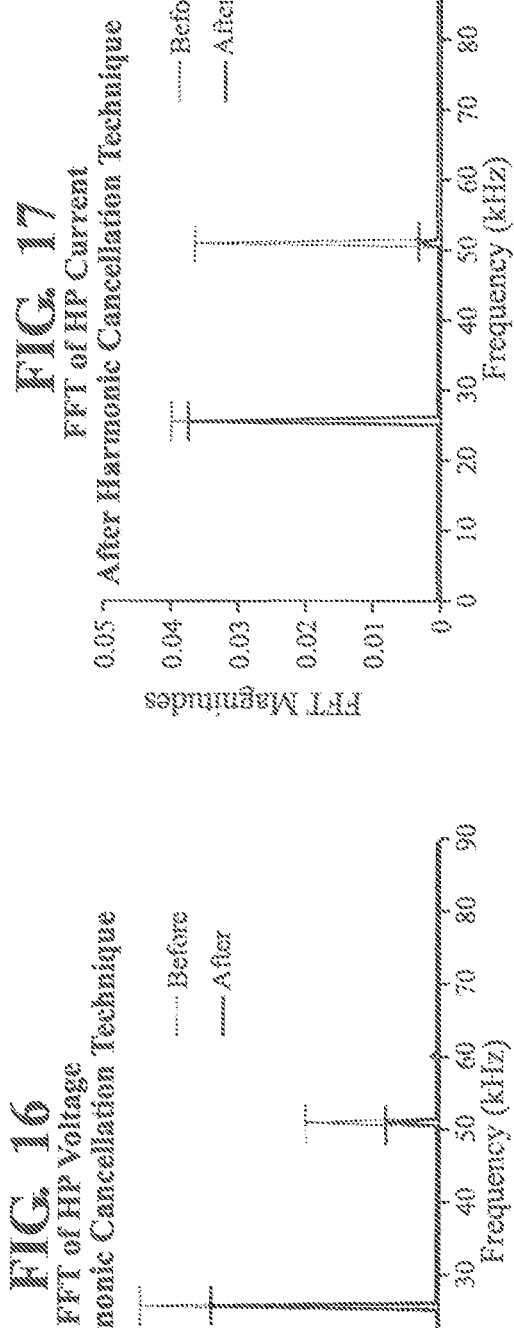
FIG. 16 is a diagram of a fast-Fourier transform of the waveform of the handpiece voltage of FIG. 18.
Figure 17:
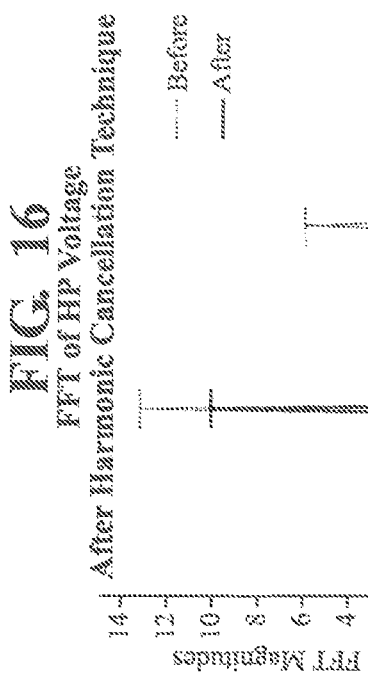
FIG. 17 is a diagram of a fast-Fourier transform of the waveform of the handpiece current of FIG. 18.
Figure 18:
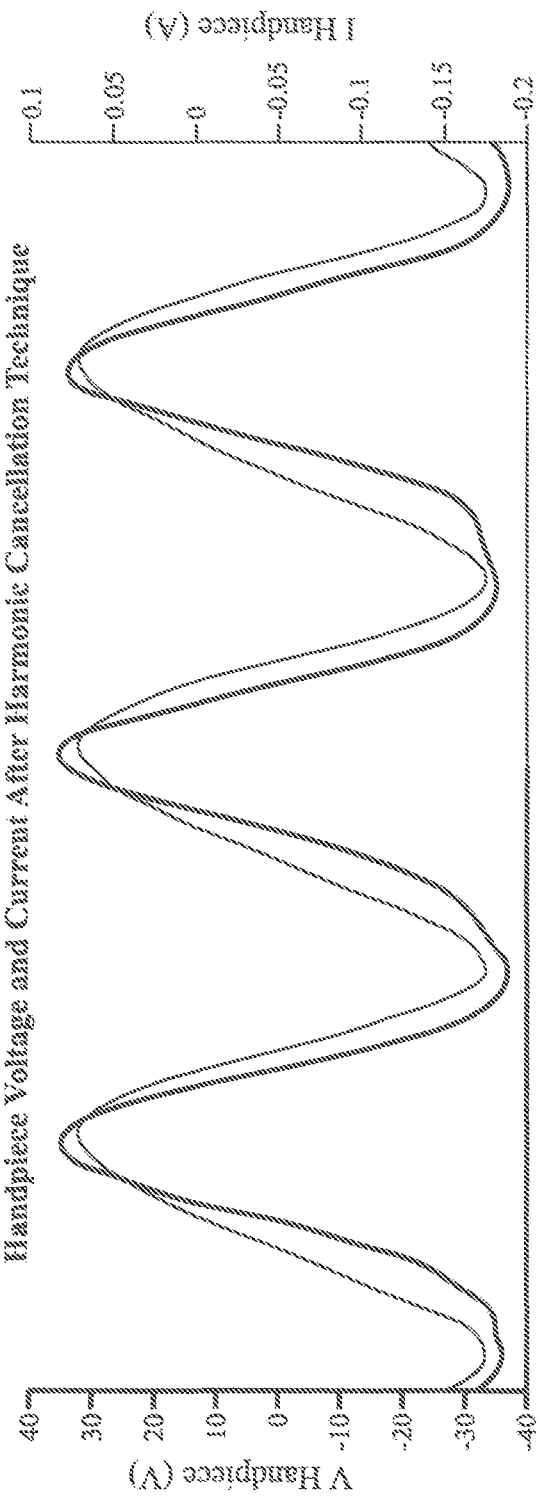
FIG. 18 is a chart of waveforms of the voltage and current of the handpiece resulting from the second drive signal of FIG. 15 after application of the harmonic cancellation method.

FIGS. 16 and 17 illustrate the respective fast-Fourier analyses for each of the waveforms for the modified handpiece voltage $V_{HP'}$ and handpiece current $i_{HP'}$ from FIG. 15. In comparison with FIGS. 6 and 7, FFT analysis reveals that the fundamental driving frequency 41 component (i.e., 25.5 kHz) is substantially unaffected by the harmonic frequency 43 component from the harmonic signal 44 (e.g., 51 kHz). Moreover, the magnitude of the harmonic frequency 43 component at 51 kHz is reduced. For the handpiece voltage $V_{HP'}$, the magnitude of the harmonic frequency 43 component is 25% of the magnitude of the harmonic frequency 43 component resulting from the first drive signal 40. For the handpiece current $i_{HP}$, the magnitude of the harmonic frequency 43 component is virtually eliminated.

Additionally, minimizing distortion in the handpiece current $i_{HP}$ may be prioritized over minimizing distortion in the handpiece voltage $V_{HP}$ since the mechanical current $i_m$ is related to mechanical displacement of the tip 26. Thus, although there is more distortion in the handpiece voltage $V_{HP}$ than the handpiece current $i_{HP}$, both waveforms exhibit significant improvement at the 51 kHz frequency.

Moreover, by controlling the harmonic frequency 43 component using the method 12, there may be opportunities to implement non-linear and bi-modal control of the tip 26. In the example provided herein, the non-linear behavior is such that when the surgical tool 20 is driven with a voltage sine wave at the fundamental driving frequency 41 component, 25.5 kHz, the handpiece 21 and tip 26, in combination, vibrate at the harmonic frequency 43 component, 51 kHz. Controlling the harmonic frequency 43 component may allow dynamic control of tips 26 to provide surgeons with more access to conventionally hard to reach areas in the body. Said differently, by reducing the negative effects of the harmonic signal 41 component, the system 10 and method 12 increase versatility to use various types and shapes of ultrasonic tools and tips often exhibiting harmonic distortion. The system 10 and method 12 further allow simultaneous control over two different resonant modes of the tip 26 to increase the cutting performance (e.g. bi-modal control). Additionally, although the cancellation signal 70 reduces the harmonic signal 44, the cancellation signal 70 may be configured to introduce additional frequency components into the second drive signal 80 for effecting bi-modal control of the tool 20.

FIG. 19 provides a table demonstrating dramatic improvement in many important parameters of controlling a handpiece 21 and tip 26 combination. For example, the handpiece voltage $V_{HP'}$ and the handpiece current $i_{HP'}$ measured during application of the second drive signal 80 were reduced by 22-23% as compared with the handpiece voltage $V_{HP}$ and the handpiece current $i_{HP}$ measured during application of the first drive signal 40. Similarly, the impedance of the handpiece 21 and tip 26 measured during application of the second drive signal 80 were reduced by 23% as compared with the impedance of the handpiece 21 and tip 26 measured during application of the first drive signal 40. Significantly, the relative magnitude of the handpiece current $i_{HP'}$ at the 51 kHz component measured during application of the second drive signal 80 was virtually eliminated, i.e., reduced by 98.8%, as compared with during application of the first drive signal 40. Additionally, in this example, the unwanted mechanical current $i_x$ present at 51 kHz after application of the second drive signal 80 was 3.4 mA. This is significantly lower than the unwanted mechanical current $i_x$ present at 51 kHz after application of the first drive signal 40, which was 83 mA, thereby showing a significant reduction in the unwanted vibration.

These results clearly demonstrate that the system 10 and method 12 effectively reduce presence of the harmonic signal 44 thereby reducing harmonic distortion occurring from vibration of the surgical tool 20. By doing so, the system 10 and method 12 have clearly reduce impedance of the surgical tool 20, the power and the voltage required for maintaining a specific vibrational displacement of the tip 26, heating of the tip 26, the energy being sent back to the console 22, and the harmonic frequency 43 component. In turn, the system 10 and method 12 drastically improve tissue resection performance of the surgical tool 20.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the present invention may be practiced otherwise than as specifically described.

The many features and advantages of the present invention are apparent from the detailed specification, and thus, it is intended by the appended claims to cover all such features and advantages of the present invention which fall within the true spirit and scope of the invention. Further, since numerous modifications and variations will readily occur to those skilled in the art, it is not desired to limit the present invention to the exact construction and operation illustrated and described, and accordingly, all suitable modifications and equivalents may be resorted to, falling within the scope of the present invention.

What is claimed is:

1. A console for controlling an ultrasonic surgical tool to reduce presence of a harmonic signal, the console comprising:
a controller configured to:
drive the ultrasonic surgical tool with a first drive signal;
acquire characteristics of the harmonic signal in the ultrasonic surgical tool resulting from driving the ultrasonic surgical tool with the first drive signal;
generate a cancellation signal based on the acquired characteristics of the harmonic signal;
combine the cancellation signal with the first drive signal to produce a second drive signal;
drive the ultrasonic surgical tool with the second drive signal;
compare the presence of the harmonic signal within a current of the ultrasonic surgical tool resulting from driving the ultrasonic surgical tool with the second drive signal to a predetermined threshold; and
based on the comparison, generate and drive the ultrasonic surgical tool with a third drive signal that reduces the presence of the harmonic signal within the current of the ultrasonic surgical tool relative to the presence of the harmonic signal within the current of the ultrasonic surgical tool resulting from driving the ultrasonic surgical tool with the second drive signal.

2. The console of claim 1, wherein the controller is configured to generate and drive the ultrasonic surgical tool with the third drive signal responsive to the comparison indicating that the presence of the harmonic signal within the current of the ultrasonic surgical tool resulting from driving the ultrasonic surgical tool with the second drive signal is greater than the predetermined threshold.

3. The console of claim 1, wherein the presence of the harmonic signal within a voltage across the ultrasonic surgical tool resulting from driving the ultrasonic surgical tool with the second drive signal is greater than the predetermined threshold, and the controller is configured to continue to drive the ultrasonic surgical tool with the second drive signal responsive to the comparison indicating that the harmonic signal within the current of the ultrasonic surgical tool resulting from driving the ultrasonic surgical tool with the second drive signal is less than the predetermined threshold.

4. The console of claim 1, wherein the predetermined threshold is 5% of a fundamental frequency component of the current of the ultrasonic surgical tool resulting from driving the ultrasonic surgical tool with the second drive signal.

5. The console of claim 1, wherein the controller is configured to: determine the current and a voltage of the ultrasonic surgical tool resulting from driving the ultrasonic surgical tool with the first drive signal; and compare the determined current and voltage to acquire at least one of the characteristics of the harmonic signal resulting from driving the ultrasonic surgical tool with the first drive signal.

6. The console of claim 5, wherein the controller is configured to:
separate a fundamental frequency component from the determined voltage;
separate a harmonic frequency component from the determined current;

determine a phase difference between the separated fundamental frequency component and the separated harmonic frequency component; and generate the cancellation signal based on the determined phase difference.

7. The console of claim 1, wherein the controller is configured to:

measure the current of the ultrasonic surgical tool resulting from driving the ultrasonic surgical tool with the first drive signal;

determine an amplitude of a harmonic frequency component of the measured current; and generate the cancellation signal with an amplitude determined based on the amplitude of the harmonic frequency component of the measured current.

8. The console of claim 7, wherein the controller is configured to generate the cancellation signal with the amplitude of the cancellation signal being twice the amplitude of the harmonic frequency component of the measured current.

9. A method for controlling an ultrasonic surgical tool to reduce presence of a harmonic signal, the method comprising:

driving the ultrasonic surgical tool with a first drive signal;

acquiring characteristics of the harmonic signal in the ultrasonic surgical tool resulting from driving the ultrasonic surgical tool with the first drive signal;

generating a cancellation signal based on the acquired characteristics of the harmonic signal;

combining the cancellation signal with the first drive signal to produce a second drive signal;

driving the ultrasonic surgical tool with the second drive signal;

comparing the presence of the harmonic signal within a current of the ultrasonic surgical tool resulting from driving the ultrasonic surgical tool with the second drive signal to a predetermined threshold; and based on the comparison, generating and driving the ultrasonic surgical tool with a third drive signal that reduces the presence of the harmonic signal within the current of the ultrasonic surgical tool relative to the presence of the harmonic signal within the current of the ultrasonic surgical tool resulting from driving the ultrasonic surgical tool with the second drive signal.

10. The method of claim 9, further comprising:

determining that the presence of the harmonic signal within the current of the ultrasonic surgical tool resulting from driving the ultrasonic surgical tool with the second drive signal is greater than the predetermined threshold; and generating and driving the ultrasonic surgical tool with the third drive signal responsive to the determination.

11. The method of claim 9, wherein the presence of the harmonic signal within a voltage across the ultrasonic surgical tool resulting from driving the ultrasonic surgical tool with the third drive signal is greater than the predetermined threshold, and further comprising:

determining that the presence of the harmonic signal within the current of the ultrasonic surgical tool resulting from driving the ultrasonic surgical tool with the third drive signal is less than the predetermined threshold; and continuing to drive the ultrasonic surgical tool with the third drive signal based on the determination.

12. The method of claim 9, wherein the predetermined threshold is 5% of a fundamental frequency component of the current of the ultrasonic surgical tool resulting from driving the ultrasonic surgical tool with the second drive signal.

13. The method of claim 9, further comprising:

determining the current and a voltage of the ultrasonic surgical tool resulting from driving the ultrasonic surgical tool with the first drive signal; and comparing the determined current and voltage to acquire at least one of the characteristics of the harmonic signal resulting from driving the ultrasonic surgical tool with the first drive signal.

14. The method of claim 13, further comprising:

separating a fundamental frequency component from the determined voltage;

separating a harmonic frequency component from the determined current;

determining a phase difference between the separated fundamental frequency component and the separated harmonic frequency component; and generating the cancellation signal based on the determined phase difference.

15. The method of claim 9, further comprising:

measuring the current of the ultrasonic surgical tool resulting from driving the ultrasonic surgical tool with the first drive signal;

determining an amplitude of a harmonic frequency component of the measured current; and generating the cancellation signal with an amplitude determined based on the amplitude of the harmonic frequency component of the measured current.

16. The method of claim 15, further comprising generating the cancellation signal with the amplitude of the cancellation signal being twice the amplitude of the harmonic frequency component of the measured current.

* * * * *